(12) United States Patent
Krimsky

(10) Patent No.: US 10,327,853 B2
(45) Date of Patent: Jun. 25, 2019

(54) SYSTEM AND METHOD OF PERFORMING TREATMENT ALONG A LUMEN NETWORK

(71) Applicant: COVIDIEN LP, Mansfield, MA (US)

(72) Inventor: William S. Krimsky, Bel Air, MD (US)

(73) Assignee: COVIDIEN LP, Mansfield, MA (US)

( * ) Notice: Subject to any disclaimer, the term of this patent is extended or adjusted under 35 U.S.C. 154(b) by 420 days.

(21) Appl. No.: 15/150,655

(22) Filed: May 10, 2016

(65) Prior Publication Data

US 2017/0325894 A1 Nov. 16, 2017

(51) Int. Cl.
A61B 18/00 (2006.01)
A61N 5/10 (2006.01)
A61B 34/20 (2016.01)
A61B 18/02 (2006.01)
A61B 18/14 (2006.01)
(Continued)

(52) U.S. Cl.
CPC ............ A61B 34/20 (2016.02); A61B 1/00 (2013.01); A61B 18/02 (2013.01); A61B 18/1492 (2013.01); A61B 18/1815 (2013.01); A61B 34/10 (2016.02); A61B 34/25 (2016.02); A61K 48/0075 (2013.01); A61M 25/0105 (2013.01); A61N 5/1002 (2013.01); A61N 5/1049 (2013.01); A61B 2018/00541 (2013.01); A61B 2018/00577 (2013.01); A61B 2018/00898 (2013.01); A61B 2018/00982 (2013.01); A61B 2018/00994 (2013.01); A61B 2034/107 (2016.02); A61B 2034/2051 (2016.02); A61B 2090/364 (2016.02); A61B 2090/368 (2016.02); A61M 2025/0166 (2013.01); A61N 2005/1024 (2013.01)

(58) Field of Classification Search
CPC .......... A61B 2018/00541; A61B 2018/00994; A61B 34/20; A61N 5/10–5/1029
See application file for complete search history.

(56) References Cited

U.S. PATENT DOCUMENTS 6,364,855 B1 4/2002 Zappala
6,493,589 B1 12/2002 Medhkour et al.
(Continued)

FOREIGN PATENT DOCUMENTS

WO 2015074018 A1 5/2015

OTHER PUBLICATIONS

International Search Report corresponding to PCT/US2017/027426, completed Jul. 5, 2017 and dated Jul. 24, 2017; (10pp).

*Primary Examiner* — Thaddeus B Cox

(57) ABSTRACT

Disclosed are systems, devices, and methods for performing treatment along a lumen network, an exemplary method comprising receiving image data of a patient's lungs, mapping one or more luminal networks inside the patient's lungs based on the received image data, identifying a treatment target in the image data, determining a luminal pathway to the treatment target via at least one of the luminal networks, configuring treatment parameters for treatment of the treatment target and at least one of the luminal networks, navigating a tool inside at least one of the luminal networks to the treatment target, treating the treatment target with a primary treatment modality, and treating the luminal pathway of at least one of the luminal networks leading to or from the treatment target with a secondary treatment modality.

11 Claims, 5 Drawing Sheets

(51) Int. Cl.
| | |
|---|---|
| *A61B 18/18* | (2006.01) |
| *A61K 48/00* | (2006.01) |
| *A61M 25/01* | (2006.01) |
| *A61B 1/00* | (2006.01) |
| *A61B 34/00* | (2016.01) |
| *A61B 34/10* | (2016.01) |
| *A61B 90/00* | (2016.01) |

(56) References Cited

U.S. PATENT DOCUMENTS

| | | |
|---|---|---|
| 6,679,824 B1 | 1/2004 | Reed et al. |
| 6,846,282 B1 | 1/2005 | Ford |
| 6,847,838 B1 | 1/2005 | Macey et al. |
| 6,994,688 B2 | 2/2006 | Brauckman et al. |
| 7,131,942 B2 | 11/2006 | Taylor et al. |
| 8,162,812 B2 | 4/2012 | Shai et al. |
| 8,808,280 B2 | 8/2014 | Mayse et al. |
| 2009/0093668 A1 | 4/2009 | Marten et al. |
| 2016/0000302 A1 | 1/2016 | Brown et al. |
| 2016/0051221 A1* | 2/2016 | Dickhans ............ A61B 8/0841 600/424 |
| 2016/0120521 A1* | 5/2016 | Weingarten ............ A61B 6/463 600/424 |

* cited by examiner

SYSTEM AND METHOD OF PERFORMING TREATMENT ALONG A LUMEN NETWORK

BACKGROUND

Technical Field

The present disclosure relates to the treatment of tissue along airway, vascular, lymphatic (AVL) lumens, and more particularly, to systems, devices, and methods for providing treatment for lung cancer along AVL lumens either as a primary treatment method, or as an adjunct treatment along with other treatment methods.

Description of Related Art

Treatment of tumors and other cancerous tissue located in or around the lungs may be accomplished by using various treatment methods, including radiation, chemotherapy, and/or various surgical procedures. Though primary treatments including surgery, radiation, and the like are good for their intended purpose, one challenge that is commonly seen is the spreading and reseeding effect. In some instances, this spreading and reseeding may be caused by the treatment intervention itself. Alternatively, the tumor, because of its connection to a variety of body networks, e.g., circulatory, respiratory, lymphatic, or biliary secretions, can spread or reseed as cells break off from the tumor and are carried through the body. One mechanism that has been described to combat the reseeding effect in microwave liver ablation using ablation needles is to treat the needle track formed by the insertion of the ablation needle following treatment of the tumor. This continued treatment of the needle track prevents spreading of the disease along the needle track by the movement of the ablation needle itself which has come into contact with the cancerous tissue and may actually be drawing cancer cells away from the tumor during the removal of the ablation needle. While such techniques are amenable to the relatively solid mass of the liver, treatment within the lungs requires additional mechanisms to achieve the desired prevention of reseeding and spread of cancerous cells within the multiple luminal networks found in the lungs.

SUMMARY

Provided in accordance with the present disclosure is a method of performing treatment along a lumen network. In an aspect of the present disclosure, the method includes receiving image data of a patient's lungs, mapping one or more luminal networks inside the patient's lungs based on the received image data, identifying a treatment target in the image data, determining a luminal pathway to the treatment target via at least one of the luminal networks, configuring treatment parameters for treatment of the treatment target and at least one of the luminal networks, navigating a tool inside at least one of the luminal networks to the treatment target, treating the treatment target with a primary treatment modality, and treating the luminal pathway of at least one of the luminal networks leading to or from the treatment target with a secondary treatment modality.

In another aspect of the present disclosure, the method further includes displaying guidance for treating the luminal pathway of at least one of the luminal networks leading to or from the treatment target with the secondary treatment modality.

In a further aspect of the present disclosure, the guidance indicates a progress of treatment.

In a further aspect of the present disclosure, the guidance includes a treatment zone based on the configured treatment parameters.

In a further aspect of the present disclosure, the one or more luminal networks are selected from the group consisting of the patient's pulmonary, vascular, and lymphatic networks.

In another aspect of the present disclosure, the method further includes tracking locations of the tool as the tool is navigated inside at least one of the luminal networks.

In a further aspect of the present disclosure, the method further includes determining a second luminal pathway to the treatment target via at least one of the luminal networks, and treating the second luminal pathway of at least one of the luminal networks leading to or from the treatment target with the secondary treatment modality.

In another aspect of the present disclosure, the primary treatment modality is selected from the group consisting of microwave ablation therapy, radio frequency ablation therapy, chemotherapy, radiation therapy, surgery, cryotherapy, gene therapy, and high dose radiation brachytherapy.

In a further aspect of the present disclosure, the secondary treatment modality is selected from the group consisting of microwave ablation therapy, radio frequency ablation therapy, chemotherapy, radiation therapy, surgery, cryotherapy, gene therapy, and high dose radiation brachytherapy.

Provided in accordance with the present disclosure is a system of performing treatment along a lumen network. In an aspect of the present disclosure, the system includes a navigation catheter insertable into at least one luminal network, a tool configured for insertion into the navigation catheter and navigating inside at least one luminal network, a sensor operatively associated with the tool or navigation catheter, an electromagnetic tracking system configured to track the sensor as the navigation catheter is navigated inside at least one luminal network, a display configured to display a user interface including image data showing the tracked locations of the sensor, a primary treatment modality insertable into the navigation catheter and configured to treat a treatment target, and a secondary treatment modality insertable into the navigation catheter and configured to treat a lumen leading to or from a treatment target.

In another aspect of the present disclosure, the at least one luminal network is selected from the group consisting of a patient's pulmonary, vascular, and lymphatic networks.

In a further aspect of the present disclosure, the display is further configured to display a pathway leading to or from a treatment target.

In another aspect of the present disclosure, the display is further configured to display a second pathway leading to or from a treatment target, and the secondary treatment modality is configured to treat a luminal network along at least a portion of the second pathway.

In a further aspect of the present disclosure, the primary treatment modality is selected from the group consisting of microwave ablation therapy, radio frequency (RF) ablation therapy, chemotherapy, radiation therapy, surgery, cryotherapy, gene therapy, and high dose radiation brachytherapy.

In another aspect of the present disclosure, the secondary treatment modality is selected from the group consisting of microwave ablation therapy, radio frequency (RF) ablation therapy, chemotherapy, radiation therapy, surgery, cryotherapy, gene therapy, and high dose radiation brachytherapy.

Provided in accordance with the present disclosure is a non-transitory computer-readable storage medium storing instructions which, when executed by a computer, cause the computer to receive image data of a patient's lungs, determine a location of one or more luminal networks inside the patient's lungs based on the received image data, identify a treatment target in the image data, determine a luminal pathway to the treatment target via at least one of the luminal networks, configure treatment parameters for treatment of the treatment target and at least one of the luminal networks, provide instructions to navigate a tool inside at least one of the luminal networks, provide instructions to treat the treatment target with a primary treatment modality, and provide instructions to treat the luminal pathway of at least one of the luminal networks leading to or from the treatment target with the secondary treatment modality.

In another aspect of the present disclosure, the instructions further cause the computer to display a progress of treatment.

In a further aspect of the present disclosure, treatment of the one or more luminal networks includes treatment of one or more of the patient's pulmonary, vascular, and lymphatic networks.

In another aspect of the present disclosure, the instructions further cause the computer to track locations of the tool as the tool is navigated inside at least one of the luminal networks.

In a further aspect of the present disclosure, the instructions further cause the computer to determine a second luminal pathway to the treatment target via at least one of the luminal networks, and provide instructions to treat the second luminal pathway of at least one of the luminal networks leading to or from the treatment target with the secondary treatment modality.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure is directed to devices, systems, and methods for providing treatment for lung cancer along AVL lumens. Treatment along AVL lumens according to the present disclosure may be performed either as a primary treatment method, or as an adjunct treatment along with other treatment methods, such as stereotactic body radiotherapy, surgery, and/or bronchoscopically delivered therapy to the primary treatment region.

Figure 4:
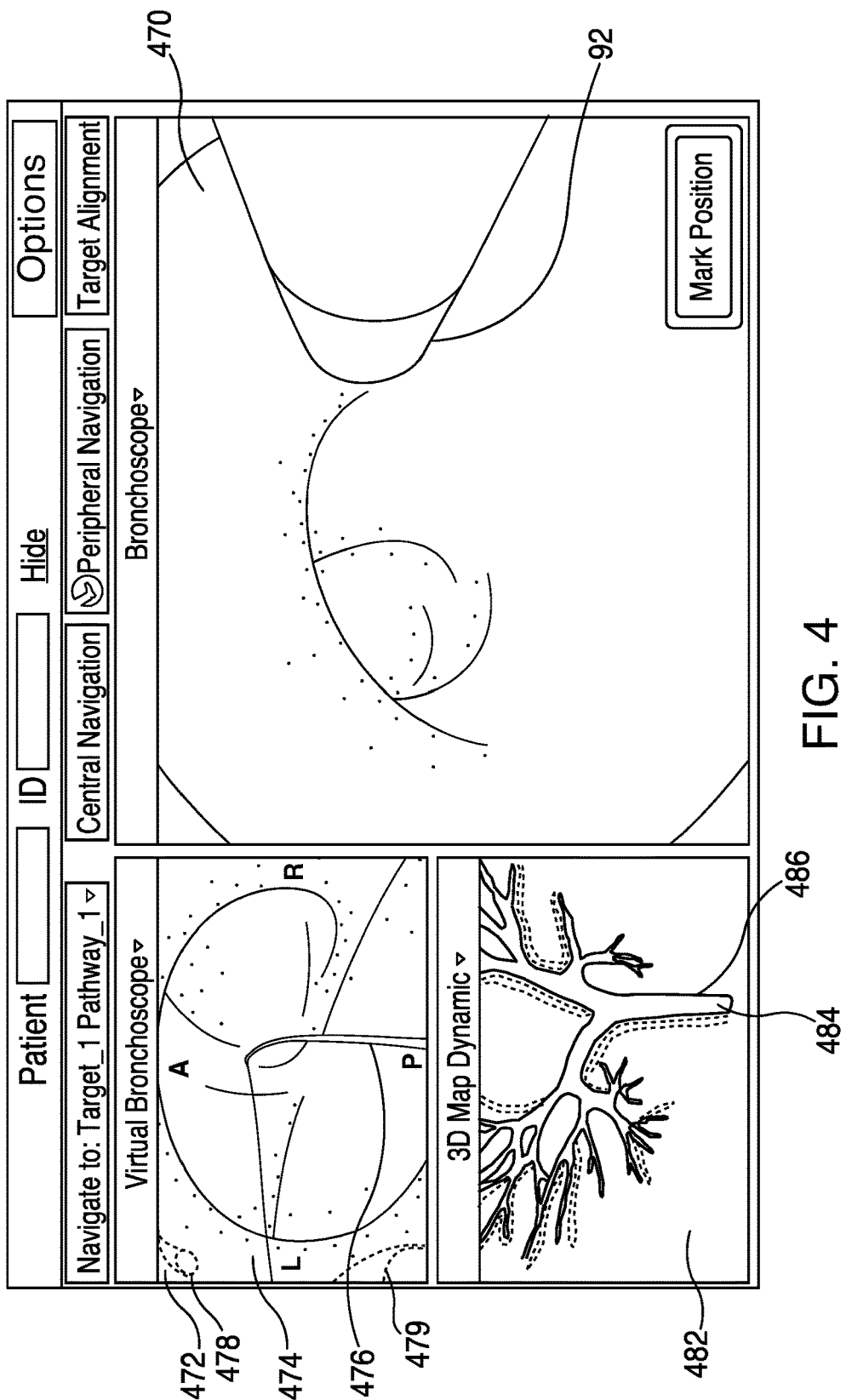
FIG. 4 is an example user interface which may be displayed by the computing device of FIG. 2, according to an embodiment of the present disclosure.

In the lungs, the airway, vascular, and lymphatic lumens generally, though not always, follow the same path, and thus are located in close proximity to each other. Such airway, vascular, and lymphatic lumens form part of the larger pulmonary, vascular, and lymphatic networks in a patient's body. When the AVL lumens are located in close proximity to each other, they may collectively be referred to as an AVL bundle. Thus, identifying the location of one of these networks will correspondingly identify the location of one or both of the others. The three networks comprising the AVL tree all converge into larger, trunk lumens at the hilum, also called the root of the lung. The airways converge into the trachea, while the vasculature converges into the pulmonary and bronchial arteries and veins. Thus, nearly all air, blood, and lymph flowing into or out of the lungs will pass through the hilum. FIG. 4 shows an example user interface including a 3D map depicting the AVL bundle in image 482 and the vascular lumen 478 and lymphatic lumen 479 largely coincident with the airways 484. It is the general commonality of location upon which the present disclosure relies to improve the described treatment along these luminal pathways.

One of the chief mechanisms by which tumors and cancer cells spread through the body is via direct angio-lymphatic invasion that is along the pathways of the AVL bundle. While localized treatment has seen success in treating particular tumors, such localized treatment is less likely to be able to fully target and capture exit pathways whereby cancerous cells may spread and reseed from the primary treatment site. The ability to treat these exit pathways from or near the edge of the primary treatment site back through to, and potentially including, the hilum and the lymph nodes that subtend them results in substantive improvement in both local control of the breakup of cancerous cells and tumors, as well as decrease the likelihood of more distant spread of such cancerous cells during and/or after treatment, thus improving the durability of the treatment. Systems, devices, and methods for providing such treatment via the AVL bundle will now be described.

Over time, as data is collected, predictive models may be developed in terms of appropriate airways and/or distributions of AVL bundles that are most likely to lead to distant spread of cancerous cells, depending on the type of tissue treated and the treatment method applied at the primary treatment site. Further, treatment along the AVL bundle could be leveraged to transition from a localized treatment method to a systemic effect, such as through the abscopal effect, especially since a potentially higher quantity of lymphatics are included in the treatment zone. As described below, treatment along the AVL bundle requires identifying locations of the pulmonary, vascular, and lymphatic networks around a treatment site, and access pathways to airway, vascular, and lymphatic lumens surrounding the primary treatment prior to the start of treatment at the primary treatment site.

An AVL bundle treatment procedure generally involves at least two phases: (1) planning one or more pathways to a treatment target located within, or adjacent to, the patient's lungs; and (2) navigating a probe to the target site along the planned pathways. These phases are generally referred to as (1) "planning" and (2) "navigation." While the disclosure of the present application is directed to treatment of the AVL bundle, systems, devices, and methods for Electromagnetic Navigation (EMN) including a method known as an ELECTROMAGNETIC NAVIGATION BRONCHOSCOPY® (ENB) procedure, which is a registered trademark of COVIDIEN LP, may also be used to perform the planning and navigation phases of the AVL bundle treatment procedure because, as mentioned above, the vascular and lymphatic trees are closely located to, and generally follow the same paths, as the airway tree in the lungs. An example of EMN planning software for an EMN procedure which can also be used for the AVL bundle treatment described herein can be found in U.S. Patent Publication Nos. 2014/0281961, 2014/0270441, and 2014/0282216, filed by Baker et al. on Mar. 15, 2013, and entitled "PATHWAY PLANNING SYSTEM AND METHOD", the entire contents of each of which are incorporated herein by reference. Further examples of the EMN planning software can be found in commonly assigned U.S. patent application Ser. No. 14/753,288, entitled "SYSTEM AND METHOD FOR NAVIGATING WITHIN THE LUNG", filed on Jun. 29, 2015, by Brown et al., the entire contents of which are incorporated herein by reference.

Prior to the planning phase, the patient's lungs are imaged by, for example, a computed tomography (CT) scan, a magnetic resonance imaging (MRI) scan, a positron emission tomography (PET) scan, and/or other applicable methods of imaging known to those skilled in the art. For purposes of brevity, this disclosure will refer to images obtained from a CT scan, however, as noted above, CT scan images and data may be substituted with images and data obtained from other imaging modalities without departing from the scope of the present disclosure. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the AVL treatment procedure.

The application may use the CT scan image data to generate the aforementioned 3D model of the patient's lungs. The 3D model may include, among other things, a model airway tree corresponding to the actual airways of the patient's lungs, and showing the various passages, branches, and bifurcations of the patient's actual airway tree. Similarly, the 3D model may include a model vascular tree and a model lymphatic tree. Additionally, the 3D model may include lesions, markers, organs, and/or other physiological structures. Some or all of the aforementioned elements may be selectively displayed, such that the clinician may choose which elements should be displayed when viewing the 3D model.

While the CT scan image data may have gaps, omissions, and/or other imperfections included in the image data, the 3D model is a smooth representation of the patient's airway, vascular, and lymphatic trees, with any such gaps, omissions, and/or imperfections in the CT scan image data filled in or corrected. As described in more detail below, the 3D model may be viewed in various orientations. For example, if a clinician desires to view a particular section of the patient's lungs, the clinician may view the 3D model represented in a 3D rendering and rotate and/or zoom in on the particular section of the patient's lungs.

During pathway planning, a computing device (see e.g., 80, FIG. 1) utilizes computed tomographic (CT) image data for generating and viewing a 3D model of the patient's airways, enables the identification of target tissue on the 3D model (automatically, semi-automatically or manually), and allows for the selection of one or more pathways through the patient's airways to the target tissue. More specifically, the CT scans are processed and assembled into a 3D volume, which is then utilized to generate the 3D model of the patient's airways. The 3D model may be presented on a display monitor associated with computing device 80, or in any other suitable fashion. Using computing device 80, various slices of the 3D volume and views of the 3D model may be presented and/or may be manipulated by a clinician to facilitate identification of the target tissue and selection of suitable pathways through the patient's airways with access the AVL lumens surrounding the target tissue. The 3D model may also show marks of the locations where treatment has previously been performed, including the dates, times, and other identifying information regarding the treatment. Once selected, the pathways are saved for use during the treatment procedure.

Once the pathways to the AVL lumens are determined, navigation to the primary treatment site commences. An EMN system may be used in planning one or more pathways to a treatment target site, navigating a positioning assembly to the target, and navigating a variety of tools, such as a locatable guide (LG), an ablation antenna, and/or a high dose radiation (HDR) brachytherapy device to the target.

Prior to the start of the navigation phase of the AVL treatment procedure, the 3D model from the planning phase is registered with the actual lungs of the patient. One potential method of registration involves navigating an electromagnetic (EM) sensor into each lobe of the patient's lungs to at least the second bifurcation of the airways of that lobe. The position of the EM sensor is tracked during this registration phase, and the 3D model is iteratively updated based on the tracked position of the EM sensor within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. patent application Ser. No. 14/790,581 entitled "REAL-TIME AUTOMATIC REGISTRATION FEEDBACK", filed on Jul. 2, 2015, by Brown et al., the entire contents of each of which are incorporated herein by reference. While the registration process focuses on aligning the patient's actual airways with the airways of the 3D model, registration also ensures that the position of the patient's vascular and lymphatic trees are accurately determined.

Figure 1:
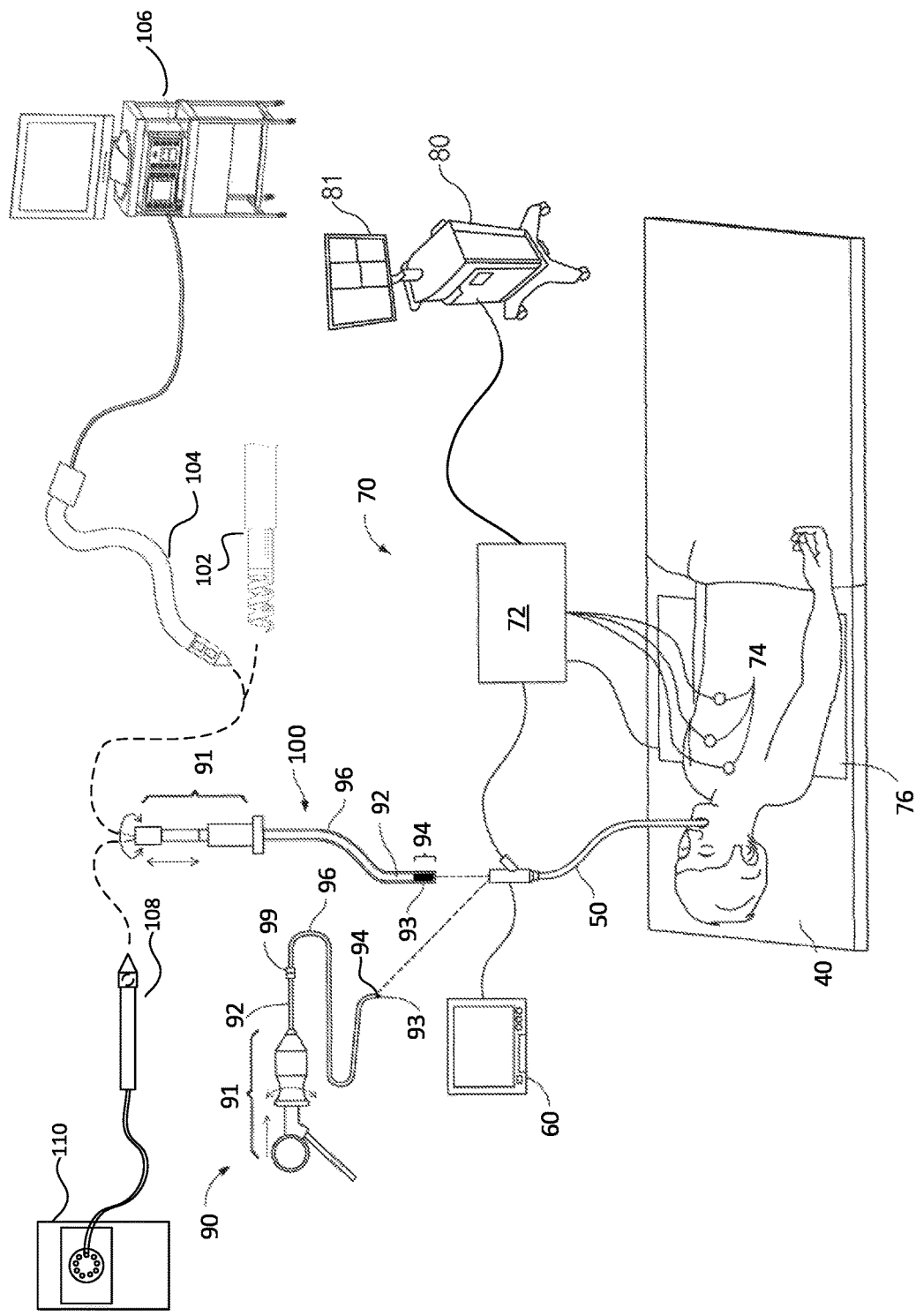
FIG. 1 is a schematic diagram of a system for performing treatment along the AVL bundle, according to an embodiment of the present disclosure.

With reference to FIG. 1, an AVL treatment system 10 is provided in accordance with the present disclosure. Among other tasks that may be performed using system 10 are determining one or more pathways to target tissue, navigating a positioning assembly to the target tissue, navigating a treatment tool to the target tissue to perform treatment of the target tissue using the treatment tool, digitally marking the location where the treatment was performed, and placing one or more echogenic markers at or around the target tissue.

System 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a computing device 80 including software and/or hardware used to facilitate pathway planning, identification of target tissue, navigation to target tissue, and digitally marking the location of the target tissue.

FIG. 1 also depicts two types of catheter guide assemblies 90, 100. Both catheter guide assemblies 90, 100 are usable with system 10 and share a number of common components. Each catheter guide assembly 90, 100 includes a handle 91, which is connected to a navigation catheter, such as extended working channel (EWC) 96. EWC 96 is sized for placement into the working channel of a bronchoscope 50. In operation, a locatable guide (LG) 92, including an electromagnetic (EM) sensor 94, is inserted into EWC 96 and locked into position such that EM sensor 94 extends a desired distance beyond a distal tip 93 of EWC 96. The location of EM sensor 94, and thus the distal end of EWC 96, within an electromagnetic field generated by electromagnetic field generator 76 can be derived by tracking module 72, and computing device 80. Catheter guide assemblies 90, 100 have different operating mechanisms, but each contain a handle 91 that can be manipulated by rotation and compression to steer distal tip 93 of LG 92 and EWC 96. An example of catheter guide assemblies 90 are those currently marketed and sold by Medtronic PLC under the name SUPERDIMENSION® Procedure Kits. Similarly, an example of catheter guide assemblies 100 are currently sold by Medtronic PLC under the name EDGE™ Procedure Kits. Both kits include a handle 91, EWC 96, and LG 92. For a more detailed description of the catheter guide assemblies 90, 100, reference is made to commonly-owned U.S. Pat. No. 9,247,992 entitled MICROWAVE ABLATION CATHETER AND METHOD OF UTILIZING THE SAME, filed on Mar. 15, 2013, by Ladtkow et al., the entire contents of which are incorporated herein by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355, entitled WIRELESS SIX-DEGREE-OF-FREEDOM LOCATOR, filed on Dec. 14, 1998, by Gilboa, and published PCT Application Nos. WO 00/10456 and WO 01/67035, the entire contents of each of which are incorporated herein by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient, as detailed below.

As shown in FIG. 1, EM field generator 76 is positioned beneath the patient. EM field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to computing device 80, which includes an application 81 that uses data collected by sensors 74 to calculate a patient coordinate frame of reference.

Although EM sensor 94 is described above as being included in LG 92 it is also envisioned that EM sensor 94 may be embedded or incorporated within a biopsy tool 102 where biopsy tool 102 may alternatively be utilized for navigation without need of LG 92 or the necessary tool exchanges that use of LG 92 requires. Similarly, it is envisioned that EM sensor 94 may be embedded or incorporated within a microwave ablation tool 104 or a brachytherapy tool 108, where microwave ablation tool 104 or brachytherapy tool 108 may alternatively be utilized for navigation without the need of LG 92 or the necessary tool exchanges that use of LG 92 requires.

During navigation, EM sensor 94, in conjunction with tracking system 70, enables tracking of EM sensor 94, and thereby LG 92 or a treatment tool, such as biopsy tool 102, microwave ablation tool 104, and/or brachytherapy tool 108, as LG 92 or one of tools 102, 104, and 108 is advanced through the patient's airways. As LG 92 or tools 102, 104, and/or 108 is navigated to a target location within the patient, the sensed location of EM sensor 94 is displayed on the computing device 80 enabling the clinician to follow the pathway that was developed during the planning phase and reach a desired target for treatment. Following arrival at the target location, the LG 92 may be removed allowing the insertion of one or more of tools 102, 104, and/or 108.

Also shown in FIG. 1 is biopsy tool 102 that is insertable into catheter guide assemblies 90, 100 following navigation to a target and removal of LG 92. Biopsy tool 102 may be used to collect one or more tissue samples from the target location and in an embodiment, is further configured for use in conjunction with tracking system 70 to facilitate navigation of biopsy tool 102 to the target location, and tracking of a location of biopsy tool 102 as it is manipulated relative to the target location to obtain the tissue sample. Similarly, microwave ablation tool 104 is configured to be insertable into catheter guide assemblies 90, 100 following navigation to a target location and removal of LG 92. Microwave ablation tool 104 is configured to be operated with a microwave generator 106, to treat tissue at the target location by, for example, using microwave energy to heat and denature proteins in the tissue resulting in coagulation and death of specific tissue. Microwave ablation tool 104 may include any of a variety of microwave ablation tools and/or catheters, examples of which are more fully described in U.S. Pat. Nos. 9,259,269; 9,247,993; and 9,044,254; and U.S. Patent Application Publication Nos. 2014/0046176 and 2014/0046211, all entitled "MICROWAVE ABLATION CATHETER AND METHOD OF USING THE SAME", filed on Mar. 15, 2013, by Ladtkow et al., the entire contents of each of which are incorporated herein by reference. Also shown is brachytherapy tool 108, which may be used to treat tissue at the target location by, for example, using HDR brachytherapy treatment such as by placing and/or moving a radioactive seed inside the patient's body. Brachytherapy tool 108 is configured to be operated with an afterloader 110 to receive radioactive material. Though shown as a biopsy tool 102, microwave ablation tool 104, and brachytherapy tool 108 in FIG. 1, those of skill in the art will recognize that other tools including for example RF ablation tools, chemotherapy tools, cryoablation tools, and others may be similarly deployed and tracked without departing from the scope of the present disclosure.

Following the primary treatment, (e.g., microwave ablation, radio frequency ablation, localized chemotherapeutic treatments, radiation therapy, surgery, cryotherapy, gene therapy, and/or high dose radiation brachytherapy) in an effort to prevent a reseeding effect, the AVL lumens leading to and from the primary treatment site receives a secondary treatment, for example, by using HDR brachytherapy, although other methods of treatment are also envisioned and those skilled in the art will appreciate that such other methods of treatment may be used without departing from the scope of the present disclosure. Such treatment along the AVL bundle leaves the airway patent but treats the cellular component of the disease that may be following these pathways to re-seed and cause the disease to spread. In another embodiment, the primary treatment may include external beam radiation, such as stereotactic body radiation therapy (SBRT) and/or image-guided radiation therapy (IGRT), treatment and/or a sublobar surgical resection. After such primary treatment, the AVL lumens may subsequently be treated with the secondary treatment, as described hereinbelow. Thus, the primary treatment and the secondary treatment need not be part of a single treatment process and may be separate treatment processes.

Figure 2A:
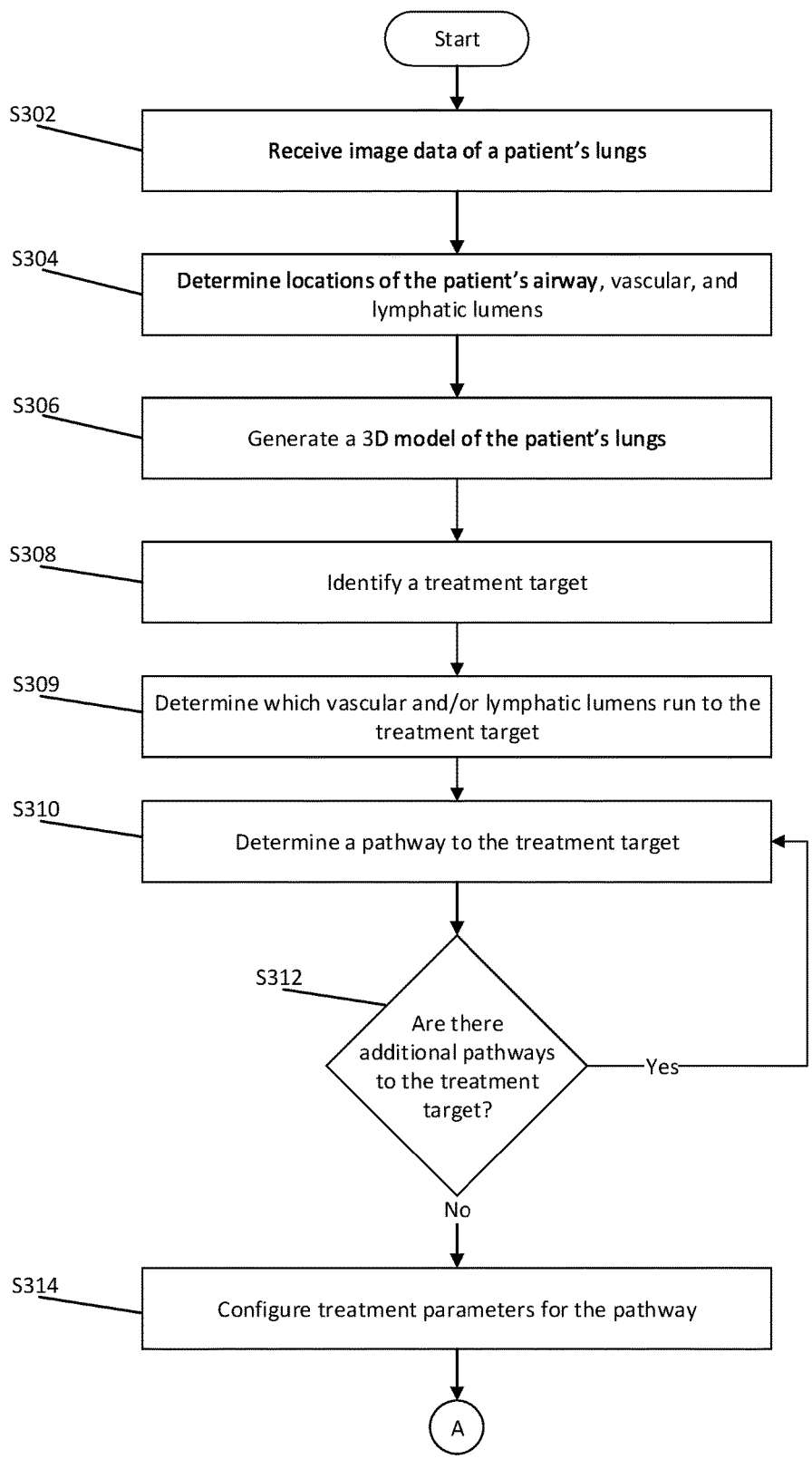
FIGS. 2A and 2B show a flowchart of an example method for performing treatment along the AVL bundle, according to an embodiment of the present disclosure.
Figure 2B:
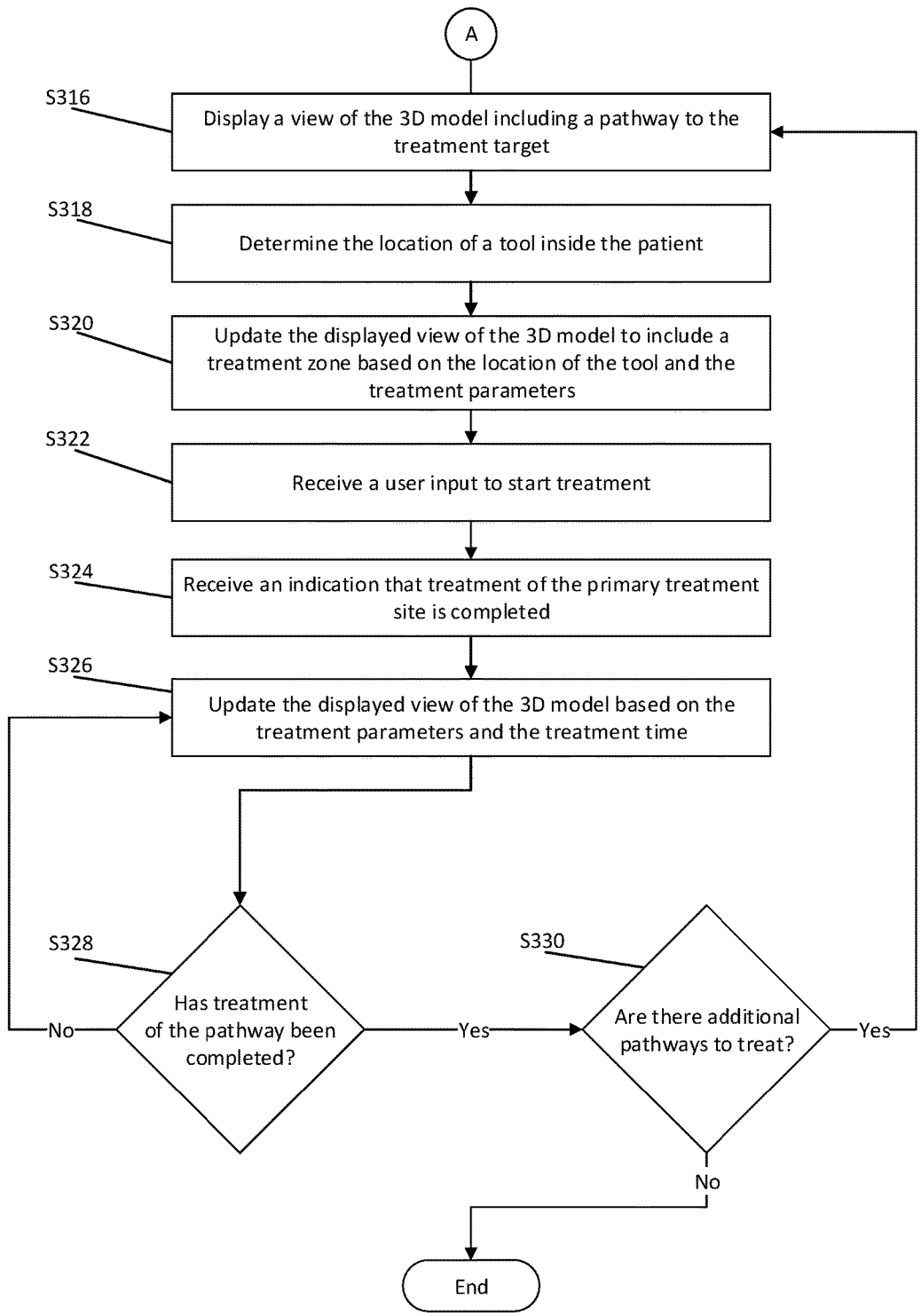

Referring now to FIGS. 2A and 2B, there is shown a flowchart of an example method for performing treatment along the AVL bundle. FIG. 2A shows the portion of the method taking place during the planning phase of the AVL treatment procedure, and FIG. 2B shows the portion of the method taking place during the navigation phase of the AVL treatment procedure.

The method may be started at step S302, where computing device 80 receives image data of the patient's lungs. As noted above, the images may be received from various imaging devices using various imaging modalities, but for illustrative purposes, this description will use CT scan data as the image data.

At step S304, application 81, executing on computing device 80, maps the locations of the patient's airway, vascular, and lymphatic trees based on the received image data. For example, application 81 may use various image processing and region growing techniques to determine the locations of the patient's AVL trees and generate a map of the patient's AVL trees based on the determined locations of the patient's AVL trees. Examples of systems, devices, and methods for using such image processing and region growing techniques are disclosed in co-pending application Ser. No. 14/821,950, entitled "TREATMENT PROCEDURE PLANNING SYSTEM AND METHOD", filed on Aug. 10, 2015, by Bharadwaj et al., and co-pending application Ser. No. 14/754,867, entitled "SYSTEM AND METHOD FOR SEGMENTATION OF LUNG", filed on Jun. 30, 2015, by Markov et al., the entire contents of each of which are incorporated herein by reference. In addition, application 81 may use data regarding the movement of the patient's airways during the patient's respiratory cycle to compensate for differences in the detected locations of the patient's AVL trees.

Thereafter, or concurrently therewith, application 81 generates the 3D model of the patient's airways, at step S306. The 3D model may be based on the image data received during step S302, image data previously stored on computing device 80, and/or previously generated 3D models of the patient. Next, at step S308, a treatment target is identified. This may be performed manually by a clinician viewing the image data and/or 3D model and marking a target location on the 3D model, or automatically using image processing techniques whereby application 81 identifies potential target locations based on the image data and 3D model. The identified treatment target and surrounding tissue will be used as the primary treatment site.

After the treatment target has been identified, application 81, at step S309, further analyzes the primary treatment site to determine which vascular and/or lymphatic lumens run to and/or through the primary treatment site. Thereafter, at step S310, application 81 determines a pathway from the target location, via the surrounding airways and reaching back to the trachea. In some embodiments, application 81 may determine a pathway starting at the trachea and proceeding to the target location. Application 81 uses the location of the identified treatment target on the 3D model and trace a pathway through the airways to the trachea. Application 81 may select the airways accompanying the vascular and/or lumens identified in step S309 as a portion of the pathway.

In some embodiments, there may be more than one vascular lumen running to and/or through the target location. Therefore, at step S312, application 81 determines whether there are additional pathways to the location of the treatment target. The additional pathways may be via airways accompanying the other vascular lumens running to and/or through the target location, and/or other airways being in close proximity to the treatment target. If application 81 determines that there are additional pathways to the location of the treatment target, processing returns to step S310, where application 81 determines another pathway to the treatment target.

If there are no additional pathways to the treatment target, processing proceeds to step S314, where treatment parameters are configured for each determined pathway. The treatment parameters may be configured manually by the clinician, and/or may be configured automatically by application 81. For example, application 81 may determine which type of treatment will be most effective given the type of target being treated and characteristics of the pathway, such as the length of the pathway, width of the lumens through which it travels, and distance between the airways and the accompanying vascular and lymphatic lumens. Other factors for determining which type of treatment will be most effective may include respirophasic changes in the orientation and diameter between the various lumens, the type of tumor or lesion being treated, and/or the state of the disease being treated. The treatment parameters may include the type of treatment, time of treatment, speed of treatment, wattage, and temperature of the treatment devices used, etc. For example, when brachytherapy tool 108 is used, the treatment parameters may include the how long the radioactive seed of brachytherapy tool 108 is uncovered, the speed at which brachytherapy tool 108 is moved through the patient's airways, and the distance which brachytherapy tool 108 should be moved before being re-covered. In another example where microwave ablation tool 104 is used, the treatment parameters may include the duration for which an ablation antenna of microwave ablation tool 104 should be activated, the time for which the antenna should be activated, the wattage at which the antenna is configured to operate, and the temperature at which the antenna is configured to operate. While brachytherapy tool 108 and microwave ablation tool 104 are mentioned here as examples, there are many other treatment methods that are also envisioned as being usable during an AVL treatment procedure, so these examples are not intended to be limiting.

The above-described steps, S302-S314, as shown in FIG. 2A, form part of the planning phase of the AVL treatment procedure. While some or all of these steps may be repeated during the navigation phase of the AVL treatment procedure, these steps will be executed at least once prior to the start of the navigation phase. Additionally, various other steps, as disclosed in the documents incorporated by reference above, may also be included in the planning phase of an AVL treatment procedure. However, these steps are the same as or similar to the steps for performing planning for an ENB procedure, such as described in the above-mentioned U.S. Patent Publication Nos. 2014/0281961, 2014/0270441, and 2014/0282216.

After completion of the planning phase of the AVL treatment procedure, the clinician may initiate the navigation phase. Similar to the above description of the planning phase, numerous steps of the navigation phase are omitted here for purposes of brevity, but are the same as or similar to the steps for performing the navigation phase of an EMN procedure, such as described in the above-mentioned U.S. patent application Ser. No. 14/753,288.

The navigation phase generally starts with application 81 displaying a view of the 3D model including a pathway to the treatment target, as described in step S316 of FIG. 2B, and shown in FIG. 4. Thereafter, bronchoscope 50, EWC 96, LG 92, and/or tools 102, 104, and 108 are inserted into the patient's airways. Subsequently, or concurrently therewith, application 81, at step S318, determines the position of EM sensor 94 inside the patient's airways, by using, for example, EM tracking system 70. Step S318 is iteratively repeated while EM sensor 94 is navigated about the patient's airways.

During the navigation phase, computing device 80 may receive additional image data of the patient's lungs, for example, from a cone beam computed tomography (CBCT) scan and/or ultrasound scan performed concurrently with, or at intervals during the navigation phase of the AVL treatment procedure. After receiving such additional image data, application 81 may update the 3D model according to the additional data. Application 81 may also update the 3D model based on data collected during the navigation phase, such as data relating to the position of EM sensor 94. Further, application 81, at step S320, may update the displayed view of the 3D model to display a treatment zone based on (1) the determined position of EM sensor 94 inside the patient's airways, and (2) the treatment parameters configured during step S314.

The treatment zone corresponds to the area that will be treated by the treatment device if treatment is performed according to the treatment parameters configured at step S314. For example, if the treatment device is brachytherapy tool 108, the treatment zone will correspond to the area of tissue surrounding the airways that will be irradiated by the radioactive seed if brachytherapy tool 108 is moved along the airways at the preconfigured speed. Similarly, if the treatment device is microwave ablation tool 104, the treatment zone will correspond to the area of tissue surrounding the airways that will be ablated by the antenna if microwave ablation tool 104 is activated based on the preconfigured parameters. In an embodiment, the treatment zone includes the vascular and lymphatic lumens accompanying the airway via which the pathway runs.

Application 81 may also use data regarding the patient's respiratory cycle to compensate for movement of the patient's airways during the various phases of the patient's respiratory cycle. For example, if application 81 determines that the patient's respiratory cycle is in a particular phase, application 81 may present an alert notifying the clinician that the currently displayed location of EM sensor 94 may be inaccurate, and suggest that the clinician not navigate further for a predetermined time until the patient's respiratory cycle is in a different phase during which the location of EM sensor 94 may be accurately displayed.

In another embodiment, if application 81 determines that the patient's respiratory cycle is in a particular phase, application 81 adjusts the displayed location of EM sensor 94 with respect to the displayed view of the 3D model based on the predetermined physiological variations of the patient's airways based on the particular phase of the patient's respiratory cycle. In yet another embodiment, if application 81 determines that the patient's respiratory cycle is in a particular phase, application 81 adjusts the displayed view of the 3D model based on the predetermined physiological variations of the patient's airways during the particular phase of the patient's respiratory cycle to compensate for the known physiological variations occurring during the particular phase of the patient's respiratory cycle such that the displayed location of EM sensor 94 remains within an airway, as displayed on the 3D model.

Steps S318 and S320 may be iteratively repeated while EM sensor 94 is navigated to the treatment target. Upon reaching the treatment target, when EM sensor 94 has been navigated proximate the treatment target and has arrived at the primary treatment site, placement of EM sensor 94 may be confirmed, such as by using a CBCT and/or fluoroscopic scan to verify that EM sensor 94 is in fact proximate the treatment target. Thereafter, at step S322, application 81 receives user input from the clinician to start treatment. As mentioned above, several methods of treatment are envisioned, and the order of treatment may vary depending on the method of treatment. For example, in some embodiments, the primary treatment site, that is, the marked location of the treatment target, may be treated first, such as by surgical procedures such as a lobectomy, resection, and/or lung volume reduction procedure, as well as other types of treatment such as radio frequency (RF) ablation, microwave ablation, chemotherapy, gene therapy, HDR brachytherapy, and/or any other relevant treatment known to those skilled in the art. The pathways to the treatment target may be treated after the treatment of the primary treatment site is complete. In another embodiment, the pathways to the treatment target may be treated first and the primary treatment site thereafter.

In yet another embodiment, the locations of vascular and/or lymphatic lumens may be identified by injecting a radiopaque substance into a treatment target and/or a lumen leading to a treatment target, and using imaging to determine which vascular and/or lymphatic lumens drain from the treatment target. For example, the locations of lymph nodes which drain to the primary treatment site may be determined, such as by using fluorescent dyes and/or other radiopaque materials. Such lymph nodes may then be used as injection sites for chemotherapy drugs and other agents that may be injected either before or after treatment of the primary treatment site. In addition, lymphatic lumens draining out of the primary treatment site may be treated using the secondary treatment method described above, and/or may be temporarily or permanently obstructed to prevent cancerous cells spreading from the primary treatment site via the lymphatic system and keep injected chemotherapy drugs localized to the primary treatment site. Using this method, directed chemotherapy treatment may be applied to both the primary treatment site and the lymph nodes leading to the primary treatment site.

Similar to the above-described method of treating the primary treatment site via the lymphatic lumens by determining the flow patterns of lumens leading to and from the primary treatment site, the vascular system my similarly be used. Directed and/or localized treatment of the primary treatment site via one or more arteries leading to the primary treatment site may be performed by injecting chemotherapy drugs into such arteries.

For illustrative purposes, an example where the primary treatment site is treated first, and the pathways to the treatment target are treated with HDR brachytherapy second is described below. At step S324, application 81 receives an indication that treatment of the primary treatment site is completed. The indication may be from the clinician manually selecting a button in application 81, or may be an automatic determination based on the treatment tool used and/or the configured treatment parameters. In some embodiments, where different methods of treatment are used for the primary treatment site and the secondary treatment of the AVL bundle, the treatment tools used for treatment of the primary treatment site may need to be removed and the treatment tools used for the secondary treatment of the AVL bundle inserted after completing treatment of the primary treatment site and before the secondary treatment may begin. For example, where the method of treating the primary treatment site uses microwave ablation tool 104, and the secondary treatment of the AVL bundle uses brachytherapy tool 108, microwave ablation tool 104 may have to be removed and brachytherapy tool 108 inserted after completion of the microwave ablation process and before starting the HDR brachytherapy treatment process. In another example, where different types of chemotherapy is used to treat the primary treatment site and the secondary treatment of the AVL bundle, the chemotherapy treatment tools may have to be switched between treatments.

Thereafter, application 81 displays a prompt for the clinician to start performing the secondary treatment. As noted above, the secondary treatment is aimed at locally treating the primary routes of spreading and/or reseeding of tumor material as a result of either the primary treatment, or which is part of the natural disease progression through the body. In an instance where the primary treatment is microwave ablation, following application of energy and adequately coagulating tissue, the secondary treatment may involve HDR brachytherapy. The secondary treatment may begin, following placement of brachytherapy tool 108 as described above, by moving the treatment tool, for example, the radioactive seed of brachytherapy tool 108, along the pathway to treat the AVL bundle. For example, this may involve moving brachytherapy tool 108 proximally from the target site towards the trachea in order to treat the distal-most tissue first (most likely to have disease bearing tissue) and to leave untreated tissue distant from the target site as deemed appropriate by the clinician.

During the movement of brachytherapy tool 108, application 81 may, at step S326, update the displayed view of the 3D model based on the treatment parameters and the treatment time. In some embodiments where EM sensor 94 is embedded in tools 102, 104, and/or 108, or a catheter such as EWC 96, the determined location of tool 102, 104, and/or 108, or EWC 96 may also be used. For example, the updated view of the 3D model may indicate the progress of the treatment of the AVL bundle. At step S328, application 81 determines, based on the configured treatment parameters and the duration of the treatment, whether the treatment of the pathway is complete. When application 81 determines that the treatment of the pathway is complete, application 81 may display an alert to the clinician to deactivate the treatment tool, such as by re-covering the radioactive seed of brachytherapy tool 108, and processing may proceed to step S330. If application 81 determines that the treatment of the pathway is not yet complete, processing returns to step S326. This determination may also be manually performed by the clinician ceasing treatment and directing the application 81 to proceed to the next step.

At step S330, application 81 determines whether there are additional pathways to be treated. If there are additional pathways to be treated, processing returns to step S316, where application 81 displays a view of the 3D model showing the next pathway to the treatment target. If application 81 determines that there are no more additional pathways to be treated, processing ends.

Though primarily described herein as using the LG 92 during navigation, EM sensor 94 may alternatively or additionally be incorporated into different types of tools that are inserted into the EWC 96, and/or incorporated into EWC 96 itself. These EM sensors 94 of the tools enable the tracking of their location and assist in navigation of the tools. As with LG 94, the tracked location of EM sensor 94 on the tool may be visually shown on a three-dimensional (3D) model of the patient's chest, and the airway, vascular, and lymphatic trees located therein. The location of EM sensor 94 within the body of the patient, with reference to the 3D model and/or 2D images as well as a planned pathway, assists the clinician in navigating about the airways and thus the AVL trees of the patient. As detailed below, tools 102, 104, and/or 108 may be further configured for use in conjunction with tracking system 70 to facilitate navigation of tools 102, 104, and/or 108 to the target tissue, tracking of a location of one or more of tools 102, 104, and 108 as it is manipulated relative to the target tissue to treat the target tissue, and/or marking the location where the target tissue is treated. FIG. 4 shows an example user interface 216 which may be displayed by application 81 during the navigation phase of the AVL treatment procedure. User interface 216 may include various views, such as a bronchoscope view 470, a virtual bronchoscope view 472, and a 3D map dynamic view 482. Bronchoscope view 470 presents the clinician with a real-time image received from the bronchoscope 50. Bronchoscope view 470 allows the clinician to visually observe the patient's airways in real-time as bronchoscope 50 is navigated through the patient's airways toward the primary treatment site.

Virtual bronchoscope view 472 presents the clinician with a 3D rendering 474 of the walls of the patient's airways generated from the 3D model. Virtual bronchoscope view 472 also presents the clinician with a navigation pathway 476 providing an indication of the direction along which the clinician will need to navigate to reach the primary treatment site. The navigation pathway 476 may be presented in a color or shape that contrasts with the 3D rendering 474 so that the clinician may easily determine the desired path to travel. Additionally, the vascular lumens accompanying the airway in which bronchoscope 50 is located may be displayed as part of the virtual bronchoscope view 472 of the 3D model, such as shown by vascular lumen 478. Similarly, the lymphatic lumens accompanying the airway in which bronchoscope 50 is located may be displayed as part of the virtual bronchoscope view 472 of the 3D model, such as shown by lymphatic lumen 479.

3D map dynamic view 482 presents a dynamic 3D model 484 of the patient's airways generated from the 3D model. The orientation of dynamic 3D model 484 automatically updates based on movement of the EM sensor 94 within the patient's airways to provide the clinician with a view of the dynamic 3D model 484 that is relatively unobstructed by airway branches that are not on the pathway to the target 452. Additionally, the vascular lumens accompanying the airway tree may be displayed as part of 3D map dynamic view 482, such as shown by vascular lumen 478. Similarly, the lymphatic lumens accompanying the airway tree may be displayed as part of 3D map dynamic view 482, such as shown by lymphatic lumen 479.

Figure 3:
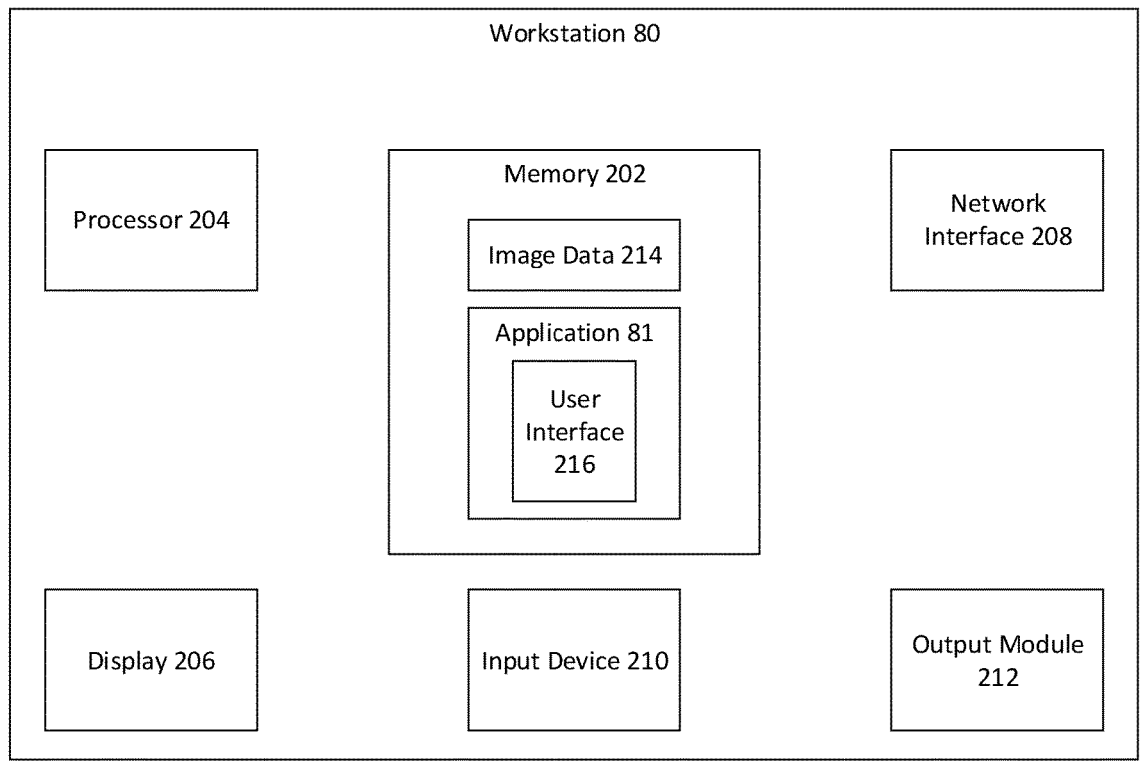
FIG. 3 is a diagram of an example computing device forming part of the system of FIG. 1, according to an embodiment of the present disclosure.

Turning now to FIG. 3, there is shown a system diagram of computing device 80. Computing device 80 may include memory 202, processor 204, display 206, network interface 208, input device 210, and/or output module 212.

Memory 202 includes any non-transitory computer-readable storage media for storing data and/or software that is executable by processor 204 and which controls the operation of computing device 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules, or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Memory 202 may store application 81 and/or CT data 214. Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with computing device 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of performing treatment along a lumen network, the method comprising:
    receiving image data of a patient's lungs;
    mapping one or more luminal networks inside the patient's lungs based on the received image data;
    identifying a treatment target in the image data;
    determining a luminal pathway to the treatment target via at least one of the luminal networks;
    configuring treatment parameters for treatment of the treatment target and at least one of the luminal networks;
    navigating a tool inside at least one of the luminal networks to the treatment target;
    treating the treatment target with a primary treatment modality, wherein the primary treatment modality is high dose radiation brachytherapy; and
    treating the luminal pathway of at least one of the luminal networks leading to or from the treatment target with a secondary treatment modality.

2. The method according to claim 1, further comprising displaying guidance for treating the luminal pathway of at least one of the luminal networks leading to or from the treatment target with the secondary treatment modality.

3. The method according to claim 2, wherein the guidance indicates a progress of treatment.

4. The method according to claim 2, wherein the guidance includes a treatment zone based on the configured treatment parameters.

5. The method according to claim 1, wherein the one or more luminal networks are selected from the group consisting of the patient's pulmonary, vascular, and lymphatic networks.

6. The method according to claim 1, further comprising tracking locations of the tool as the tool is navigated inside at least one of the luminal networks.

7. The method according to claim 1, further comprising:
    determining a second luminal pathway to the treatment target via at least one of the luminal networks; and
    treating the second luminal pathway of at least one of the luminal networks leading to or from the treatment target with the secondary treatment modality.

8. The method according to claim 1, wherein the secondary treatment modality is selected from the group consisting of microwave ablation therapy, radio frequency ablation therapy, chemotherapy, radiation therapy, cryotherapy, gene therapy, and high dose radiation brachytherapy.

9. The method according to claim 1, wherein the secondary treatment modality is high dose radiation brachytherapy.

10. The method according to claim 9, further comprising adjusting at least one of:
    a first time when a radioactive seed of a brachytherapy tool is uncovered;
    a speed at which the brachytherapy tool is moved; and
    a second time when the radioactive seed of the brachytherapy tool is recovered.

11. The method according to claim 1, wherein the secondary treatment modality is surgery.

* * * * *